(12) United States Patent
Brown

(10) Patent No.: US 7,124,518 B1
(45) Date of Patent: Oct. 24, 2006

(54) ORTHOTIC ASSEMBLY HAVING STATIONARY HEEL POST AND SEPARATE ORTHOTIC PLATE

(75) Inventor: Dennis N. Brown, Blaine, WA (US)

(73) Assignee: Northwest Podiatric Laboratory, Inc., Blaine, WA (US)

(*) Notice: Subject to any disclaimer, the term of this patent is extended or adjusted under 35 U.S.C. 154(b) by 193 days.

(21) Appl. No.: 10/982,156

(22) Filed: Nov. 5, 2004

Related U.S. Application Data

(60) Continuation-in-part of application No. 10/635,324, filed on Aug. 5, 2003, now abandoned, which is a continuation of application No. 09/575,830, filed on May 22, 2000, now Pat. No. 6,601,320, which is a division of application No. 09/179,249, filed on Oct. 26, 1998, now Pat. No. 6,125,557.

(51) Int. Cl.
*A43B 13/14* (2006.01)
*A61F 5/14* (2006.01)

(52) U.S. Cl. .......................... 36/25 R; 36/43; 36/11.5; 36/144

(58) Field of Classification Search ................ 36/25 R, 36/37, 81, 144, 15, 100, 101, 43, 44, 71, 36/11.5, 35 R, 36 R, 36 B, 42, 28
See application file for complete search history.

(56) References Cited

U.S. PATENT DOCUMENTS

| | | | | |
|---|---|---|---|---|
| 1,907,997 A | * | 5/1933 | Nickerson | 36/163 |
| 1,920,112 A | * | 7/1933 | Shaft | 36/37 |
| 2,433,329 A | * | 12/1947 | Adler et al. | 36/81 |
| 2,852,865 A | * | 9/1958 | Spalding | 36/37 |
| 2,940,187 A | * | 6/1960 | Mitchell | 36/43 |
| 3,373,513 A | * | 3/1968 | Jewell | 36/80 |
| 4,079,526 A | * | 3/1978 | Fukuoka | 36/30 R |
| 4,742,625 A | * | 5/1988 | Sydor et al. | 36/3 R |
| 4,776,109 A | * | 10/1988 | Sacre | 36/3 B |
| 4,823,420 A | * | 4/1989 | Bartneck | 12/142 N |
| 6,125,557 A | * | 10/2000 | Brown | 36/144 |
| 6,474,003 B1 | * | 11/2002 | Erickson et al. | 36/100 |
| 6,601,320 B1 | * | 8/2003 | Brown | 36/25 R |
| 2006/0032088 A1 | * | 2/2006 | Manz et al. | 36/28 |

* cited by examiner

*Primary Examiner*—Ted Kavanaugh
(74) *Attorney, Agent, or Firm*—Todd N. Hathaway

(57) ABSTRACT

An orthotic insert assembly having a stationary heel post with a guide slot and an unattached rigid plate member with a depending peg that is received in the slot. The peg cooperates with the guide slot to control and direct a medial-to-lateral rocking movement of the plate member as the wearer's foot progresses through the gait cycle. The slot may be angled to impose a predetermined direction on the rocking movement.

22 Claims, 9 Drawing Sheets

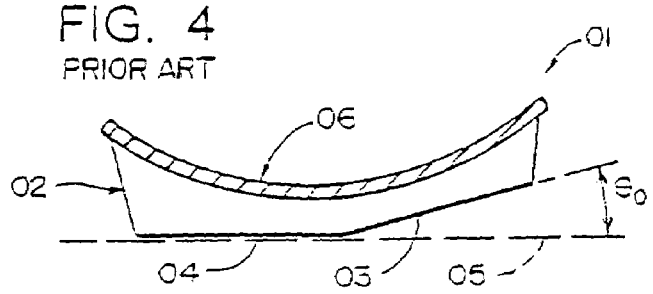
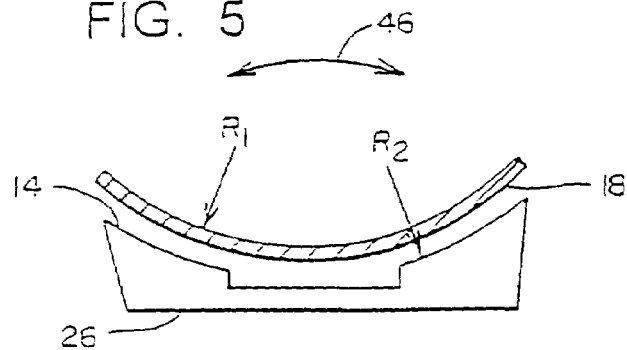
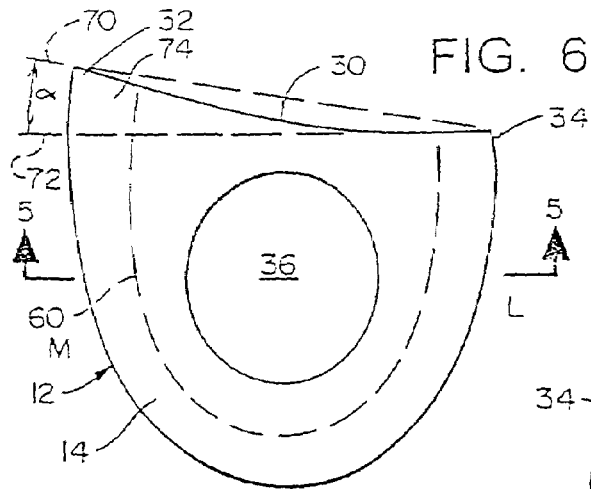
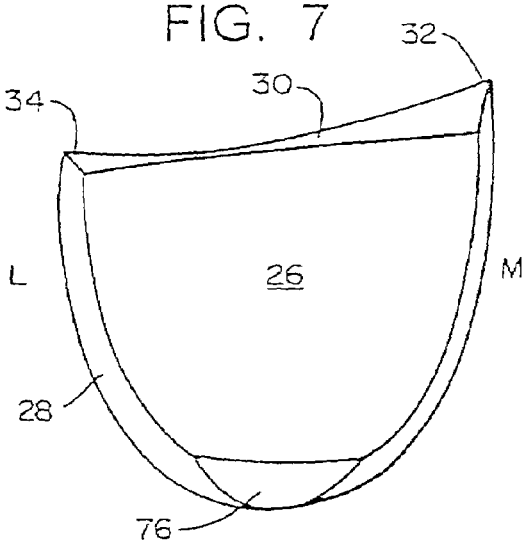

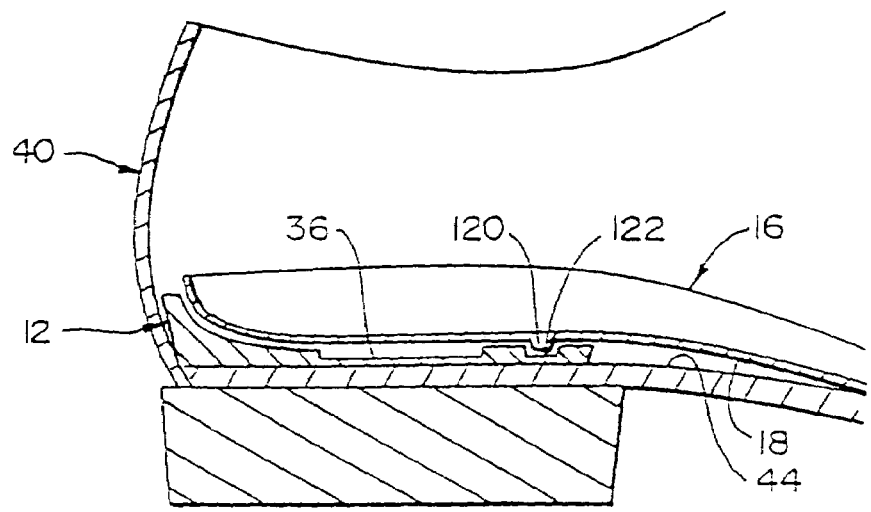
FIG. 23
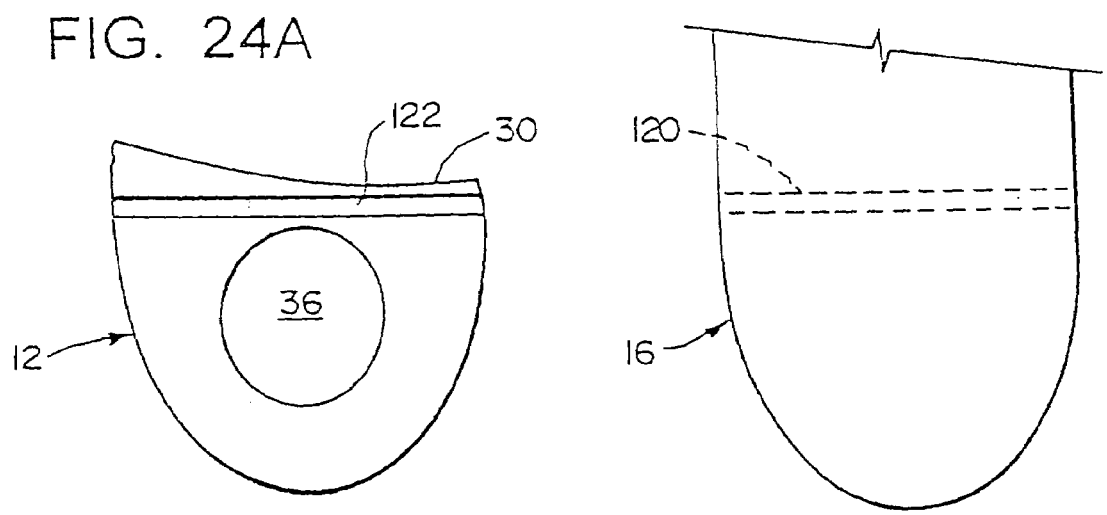
FIG. 24A
FIG. 24B

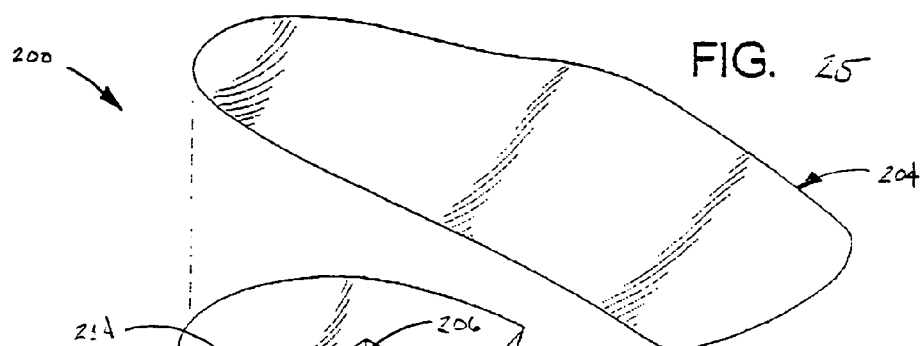
FIG. 25
FIG. 26
FIG. 27
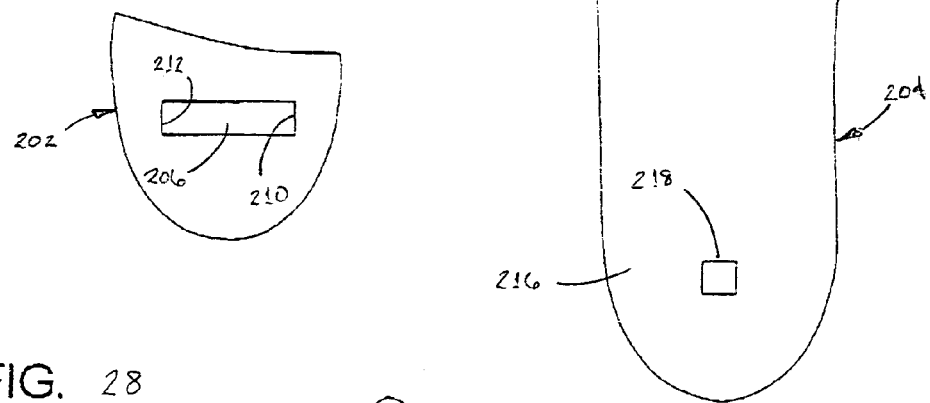
FIG. 28
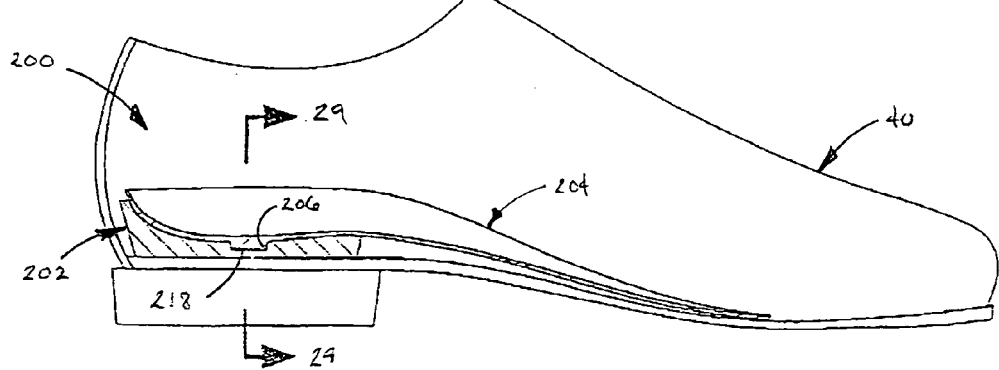

ORTHOTIC ASSEMBLY HAVING STATIONARY HEEL POST AND SEPARATE ORTHOTIC PLATE

This application is a continuation-in-part of application Ser. No. 10/635,324 filed on 5 Aug. 2003 now abandoned, which is a continuation of application Ser. No. 09/575,830, filed May 22, 2000 issued as U.S. Pat. No. 6,601,320 B1 on 5 Aug. 2003, which is a divisional of application Ser. No. 09/179,249, filed Oct. 26, 1998 issued as U.S. Pat. No. 6,125,557 on 3 Oct. 2000.

BACKGROUND OF THE INVENTION a. Field of the Invention

The present invention relates generally to orthotic devices for use in shoes, and, more particularly, to an orthotic insert in which there is a stationary heel post and a separate plate member which is pivotable thereon so as to provide a controlled range of motion for the foot.

b. Background Art

Orthotic devices have long been employed with considerable success to treat conditions or otherwise enhance the functions of the human foot, whether for ordinary walking or for various forms of specialized activities, such as skiing, skating, running and so on.

One form of such device has been a built-up structure in which there is a generally rigid, but still somewhat resiliently flexible plate, which usually extends from the heel of the foot to the metatarsal head area (i.e., the area beneath the metatarsal heads of the five phalanges), and a thick, vertical post which is fixedly mounted to the heel end of the plate. Typically, the orthotic plate is constructed of a thin, generally rigid material, such as fiberglass or graphite-resin composite, polyurethane, or a similar material, while the post is frequently formed of a hard material which is capable of supporting the rear foot under the high compressive loads which are developed at heel strike.

Such orthotic devices generally serve to both initially position the foot and then control the foot's motions as it progresses through the gait cycle, e.g., a normal foot should roll (frontal plane motion) about 4°–6° when walking, and perhaps 20°–30° when running. To control the motion of the foot, the plate member flexes resiliently to a controlled degree, and also there is often a need to impart a degree of rocking or eversion/inversion motion of the heel post as well, depending on the demands of the needs of the individuals foot/gait and the intended use. For example, for a high-impact running gait, it is often desirable to effectively increase the inversion of the rearfoot at heel contact, so as to increase the total amount of pronation and therefore the total amount of motion which is available for the balance of the gait cycle.

To adjust the rear foot angulation, and also in those instances where the heel post is supposed to move within the shoe, a common practice has been to grind off or otherwise remove material from the bottom of the heel post, in the area where this engages the insole. For example, FIG. 4 shows an exemplary prior art orthotic device 01, in which a portion of the heel post has been ground off to form a secondary planar surface 03 on the lateral underside of the post. This provides the post with a "bi-planar" bottom, so that it pivots through a controlled angle $\theta_0$, from a first position in which the main bottom surface 04 rests generally flat on the plane 05 of the insole, to a second position in which the upwardly angled surface 03 rests on the insole: For example, at heel strike the rearfoot is generally inverted and the weight is borne mostly on the lateral side of the heel, so that the secondary surface 03 is pressed against the base plane 05, and then as the foot pronates and the weight shifts forwardly and medially, the device rocks onto the main post surface 04.

The purpose of the rocking motion of the heel post is to impart this motion to the plate member 06 which is mounted to the top of the post, the plate member being the component which actually bears against and engages the plantar surface of the person's foot. For several reasons, however, the operation of such devices is frequently less than satisfactory.

For example, achieving the correct pivoting motion is highly dependent on the engagement between the bottom surface of the post and the underlying insole, but the contours of most insoles tend to be irregular and vary greatly from shoe to shoe; in an effort to provide a uniform surface for the post, some practitioners have resorted to filling in the heel area of the insole to provide a more or less flat, uniform surface, but this is an expensive and time-consuming process, and also modifies the shoe so that in some instances it can no longer be used without the orthotic.

Furthermore, the rearward portion of the device must have sufficient clearance between it and the interior of the shoe to allow for the pivoting motion (or else the edge of the device will rub against the inside of the shoe), but where the heel counter of the shoe is particularly tight it may not be possible to establish this clearance, at least without having to modify the device to the point where it is ineffective or uncomfortable to wear. Even in those instances where the heel counter is sufficiently large or loose to accommodate the device, time-consuming trimming and grinding of the device is often necessary to establish the proper motion.

Moreover, even when such devices do function as intended, the results have generally been less than ideal from a biomechanical standpoint. In particular, the pivoting motion of the post, back and forth between the two positions, is somewhat abrupt and irregular in nature, whereas a smoother, more uniform motion would be preferable from the standpoint of both function and user comfort.

Yet another problem which is inherent in conventional posted orthotic devices of the type which has been described above is that fabrication of the built-up structure is notably labor-intensive and expensive from a manufacturing perspective. As was noted above, the plate is frequently formed of a thin, hard material, such as fiberglass or graphite-fiber resin material, while the post is commonly formed of hard rubber or something similar. In order to establish a bond between these two components which will be sufficiently strong and durable to withstand repeated impacts and distortions without separating frequently requires the use of relatively specialized and expensive adhesive compounds. Moreover, extensive and painstaking surface preparation is often necessary in order for these adhesives to work properly, typically involving grinding or otherwise abrading one or both surfaces, applying both primary and final coats of adhesive, heating the components in an oven, and so on. As a result, the need to fixedly mount the post to the orthotic plate adds significantly to the cost of the product.

Accordingly, there exists a need for an orthotic device in which the motion of the plate member which engages the plantar surface of the foot is generated independently of and without being affected by any irregularities or differences in contour which may exist in the heel area of a shoe insole. Furthermore, there exists a need for such an orthotic device in which such motions in a significantly smoother, more uniformed manner. Still further, there exists a need for such an orthotic device which eliminates the need for gluing or otherwise mounting the post and orthotic plate to one another.

SUMMARY OF THE INVENTION

The present invention has solved the problems cited above, and is an orthotic insert assembly for use with a shoe having an insole, comprising (a) a post member for substantially stationary mounting in the shoe, the post member comprising an elongate guide slot on an upper side thereof; and (b) a thin, substantially rigid plate member for engaging a plantar surface of the wearer's foot in the shoe, the plate member being substantially free from attachment to the post member and comprising a heel cup formed in a heel portion thereof, and a peg portion depending from a lower surface of the heel portion for being received in the guide slot of the post member so that the peg portion cooperates with the guide slot to control and direct movement of the plate member atop the post member.

The guide slot in the post member may extend in a direction generally transverse to a long axis of the assembly, so that the peg portion on the plate member cooperates with the guide slot to control a generally lateral-to-medial rocking movement of the plate member as the wearer's foot progresses through a gait cycle.

The guide slot in the post member may comprise a substantially vertically extending forward wall for reacting against the depending peg on the plate member so as to retain the plate member against shifting forwardly in the shoe. The guide slot may further comprise a substantially vertically extending rearward wall for reacting against the depending peg portion so as to retain the plate member against shifting rearwardly in the shoe; the depending peg portion may comprise substantially vertically extending forward and rearward wall portions that bear against the vertically extending rearward and forward walls of the guide slot in face-to-face engagement therewith. The depending peg portion on the plate member may have a forward-to-rearward width approximately equal to a forward-to-rearward width of the guide slot, so that the peg portion forms a close fitting sliding interfit therewith. The guide slot may have a transverse length that is sufficient to permit lateral-to-medial rocking movement of the plate member to extend over a predetermined range, and may comprise medial and lateral end walls for engaging the depending peg portion so as to arrest movement of the plate member outside of the predetermined range.

The post member may have a generally concave upper bearing surface and the plate member may have a generally convex lower bearing surface on the heel portion for resting on the concave upper bearing surface of the post member in pivoting engagement therewith. The guide slot in the post member may comprise a bottom wall having a concave curvature that generally parallels the concavely curved upper bearing surface of the post member, and the depending peg portion may comprise a bottom end wall having a convex curvature for forming a load bearing sliding interface with the concavely curved bottom wall of the guide slot.

The guide slot may extend in a generally transverse direction that is angled to direct rocking movement of the plate member along a path that provides predetermined control over motions of the wearer's foot. The guide slot may extend in a direction that is substantially perpendicular to the long axis of the assembly, or may extend in a direction that is angled forwardly towards a medial or lateral side of the post member.

The invention also provides a method for positioning and controlling a wearer's foot in a shoe, comprising the steps of: (a) mounting a substantially stationary post member in a heel portion of a shoe, the post member comprising an elongate guide slot on an upper side thereof; and (b) placing in the shoe a thin, substantially rigid plate member for engaging the plantar surface of the wearer's foot, the plate member being substantially free from attachment to the post member and comprising a heel cup formed in a heel portion thereof, and a peg portion depending from a lower surface of the heel portion of the plate member that is received in the guide slot in the post member so that the peg portion cooperates with the guide slot to control and direct movement of the plate member atop the post member.

The invention further provides a shoe having an orthotic assembly, comprising:

(a) a post member mounted in a substantially stationary position in the shoe, the post member comprising an elongate guide slot on an upper side thereof; and (b) a thin, substantially rigid plate member for engaging the plantar surface of the wearer's foot, the plate member being substantially free from attachment to the post member and comprising a heel cup formed in a heel portion thereof, and a peg portion depending from a lower surface of the heel portion that is received in the guide slot in the post member so that the peg portion cooperates with the guide slot to control and direct movement of the plate member atop the post member.

These and other features and advantages of the invention will be more fully understood from a reading of the following detailed description with reference to the accompanying drawings.

BRIEF DESCRIPTION OF THE DRAWINGS

FIG. 4 is a cross-sectional view looking forwardly from the rear of an exemplary prior art orthotic device in which the post is fixedly mounted to the bottom of the orthotic plate;

FIG. 5 is another cross-sectional view, looking from the rear forwardly, of an orthotic assembly in accordance with the present invention, showing the two-piece construction having separate heel post and plate members, and the manner in which the plate member is free to pivot against the concave upper surface of the post member;

FIG. 6 is a top, plan view of a separate post member in accordance with the present invention, showing the generally U-shaped bearing zone on the concave upper surface of the post member, and the subcalcaneal recess which relieves contact pressures between the surfaces in the area directly beneath the heel cup;

FIG. 7 is a bottom, plan view of the post member of FIG. 6, showing the uniplanar bottom surface and the contours around the heel end thereof;

FIG. 23 is a side, cross-sectional view of the rear foot portion of a shoe and orthotic assembly in accordance with an embodiment of the present invention in which the plate member has a downwardly projecting transverse ridge which engages a corresponding groove in the post member to prevent the plate member from sliding forwardly in the shoe;

FIG. 24A is a top, plan view of the post member of the orthotic assembly of FIG. 23, showing the transverse groove which is formed in the upper surface thereof;

FIG. 24B is top, plan view of the rear foot portion of the plate member of the orthotic assembly of FIG. 23, with the dotted line image showing the downwardly projecting, transverse ridge thereon which engages the groove and the post member;

FIG. 25 is a perspective view of a two-part orthotic assembly in accordance with another embodiment of the present invention, in which the heel post is provided with a guide slot that receives a depending peg portion on the bottom of the plate member so as to control and direct the motion of the plate member;

FIG. 26 is a top, plan view of the post member of FIG. 25, showing the guide slot thereof in greater detail;

FIG. 27 is a bottom, plan view of the plate member of the orthotic assembly of FIG. 25, showing the peg portion thereof in greater detail;

FIG. 28 is an elevational, cross-sectional view showing the orthotic assembly of FIG. 25 installed in an exemplary right-foot shoe;

DETAILED DESCRIPTION a. Overview

Figure 1:
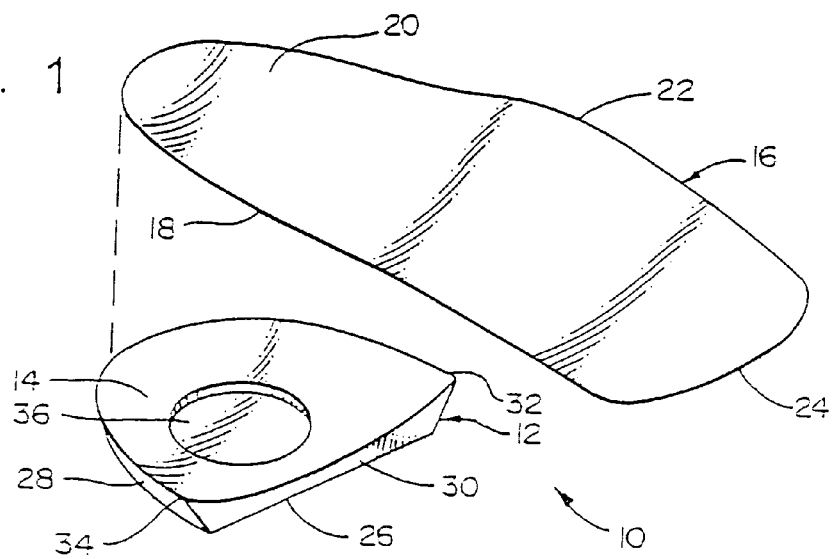
FIG. 1 is a perspective view of the two-part orthotic assembly of the present invention, showing the separate heel post and rigid plate members of the assembly.

FIG. 1 shows an orthotic assembly 10 in accordance with the present invention. As can be seen, this comprises two major components, a post member 12 having a generally concave upper surface 14, and a separate plate member 16 have a generally proximal lower surface 18 which fits into and engages the concave upper surface of the post member so as to allow a pivoting or "rocking" motion between the two pieces.

The plate member includes a heel cup area 20, the upper surface of which engages the plantar surface of the wearer's rear foot, an arch portion 22 which extends beneath the arch of the foot, and a forward end 24 which engages the plantar surface of the forefoot area; in the embodiment which is illustrated, the forward edge 24 is configured to lie generally beneath the metatarsal head area of the foot, so as to lie generally flat with the frontal plane of the foot in the later phases of the gait cycle. The plate member can be formed of any suitable, generally rigid material, with a thin, rigid, resiliently flexible material being preferred; fiberglass-resin and graphite fiber-resin materials are eminently suitable for this purpose, and cast urethane, various plastics, various metals, and other suitable materials may also be used in various embodiments. Also, although not shown in FIG. 1, the plate member may include a cushioning top cover for added wearer comfort.

The post member 12, in turn, is configured to receive and engage the rear foot portion of the plate member. As was noted above, this has a concave upper surface 14, which engages the corresponding convex surface 18 on the bottom of the plate member. The concave upper surface is located a predetermined, spaced distance above the flat, generally planar bottom surface 26 of the post member, the latter being configured to rest in a stationary position atop the insole of the shoe.

The rearward perimeter wall 28 of the post member follows a generally U-shaped contour which is configured to generally match the heel counter of the shoe, and a transverse forward wall 30 extends across the front of the member. As will be described in greater detail below, the forward wall 30 preferably extends at an angle to the long axis of the device (as opposed to being at a right angle thereto), so that the forward medial corner 32 of the post member projects to a somewhat more forward position than the lateral corner 34.

A downwardly extending recess 36 is preferably formed more or less centrally in the concave upper surface 14 of the post member, so as to be positioned generally beneath the calcaneus of the wearer's foot. As will also be described in greater detail below, this serves to reduce contact pressures beneath the plate and post members at the bottom of the heel cup, so that the plate member is supported by the top of the post member along a generally U-shaped, peripheral zone which extends around the heel end of the device, so as to facilitate the positioning of the rear foot and the pivoting motion of the plate member. A generally circular or oval recess is shown in FIG. 1, however, it will be understood that the recess may have any suitable shape, and may be open to the edge or bottom of the post member in some embodiments. Also, in some embodiments the plate may have a corresponding hole formed through it which is positioned generally in register with the underlying recess in the post member so as to completely off-load a given area of the heel, e.g., for accommodation of a heel spur or other condition of the foot.

The body of the post member may be formed of any suitable material having sufficient compressive strength to form the upper concave surface and to perform the rear foot angulation and other functions described herein, with hard rubber being eminently suitable for this purpose; in some embodiments, the post member may be formed in whole or in part of a lower durometer rubber, foam or other resiliently compressible material, so as to provide a degree of cushioning for the foot during heel strike and the initial phases of the gait cycle. It will be understood, however, that low-friction bearing surfaces will generally be preferred in order to facilitate the pivoting action of the plate member.

Figure 2:
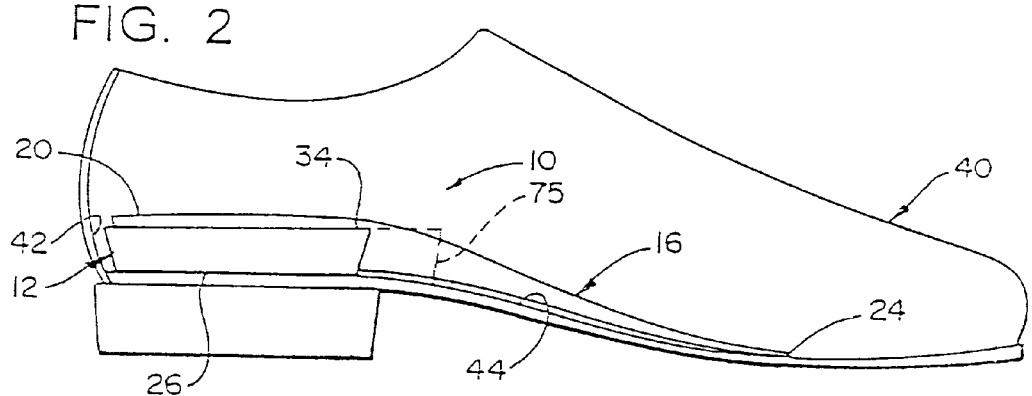
FIG. 2 is an elevational view showing the orthotic assembly of FIG. 1, as installed in an exemplary right-foot shoe.

When the assembly 10 is placed in a shoe 40 as shown in FIG. 2, the post member 12 resides in a stationary position within the heel counter 42, with its bottom surface 26 resting more-or-less flat on the insole 44. The heel cup 20 of the plate member rests within and is supported by the concave upper surface of the heel post, but remains free to pivot from side to side, i.e., to invert and evert about the long axis of the foot therein. The forward edge 24 of the plate member, in turn, rests against the insole in the forefoot area of the shoe, generally in the area beneath the metatarsal heads.

Figure 3:
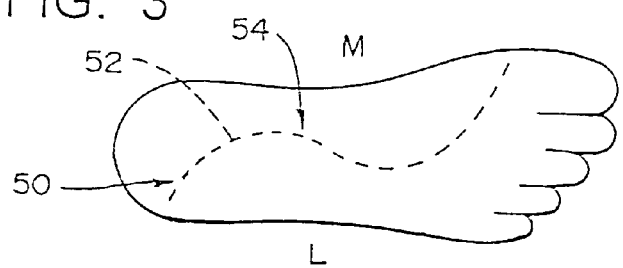
FIG. 3 is a plan, somewhat schematic view of the human foot, showing the general path which is followed by the downward weight on the foot, from the lateral side of the heel at heel strike, towards the medial side of the foot following heel strike.

As is shown in FIG. 5, the radii R1 and R2 of the surfaces 18 and 14 of the plate member and post member are selected to permit a predetermined degree of side-to-side pivoting or rocking motion to develop between the members, as indicated by arrows 46, as the wearer's foot through the gait cycle. As was noted above, and as is shown in FIG. 3, during the initial phases of the gait cycle the wearer's rear foot is generally somewhat inverted (generally, the foot is balanced when it is about 4° inverted) and the weight is borne towards the lateral side, in the area indicated generally at 50. As a result, the plate member 16 is shifted towards the right in FIG. 5 (i.e., towards the lateral aspect of the rear foot) when the heel touches down. Then, as the foot progresses into the gait cycle, the rear foot everts and the weight shifts along path 52 towards the medial side, as indicated at 54 in FIG. 3, until the medial forefoot comes down against the insole along the frontal plane of the foot (typically, at about the 25% point in the gait cycle). As a result, the plate member shifts towards the left (i.e., medial side) in FIG. 5, until the motion of the foot is arrested after a predetermined amount of pronation has occurred.

As will be described in greater detail below, the initial angulation of the rear foot is controlled by the angulation of the upper surface 14 of the host member, in particular the angulation of the general plane in which the U-shaped bearing zone lies. The amount of motion, in turn, and therefore the degree of pronation which is permitted by the device, is limited by engagement of the under surface 18 of the plate with the medial side of the concave post member, and also by the distal medial edge 24 of the plate member coming to rest against the insole of the shoe a long the frontal plane; the manner in which this range of travel can be adjusted will also be described in greater detail below.

b. Structure

FIGS. 6–11 show the structure of the heel post member 12 in greater detail.

Figure 8:
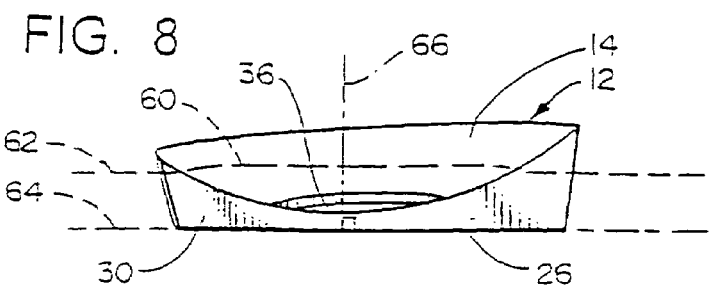
FIG. 8 is a front, elevational view of the post member of FIGS. 6–7, showing the concave upper bearing surface thereof.

Firstly, as was noted above, the main load-bearing engagement between the plate and post members follows a generally U-shaped zone around recess 36 and the heel end of the post, as indicated generally by dotted line 60 in FIGS. 6 and 8. As can be seen in FIG. 8, the U-shaped bearing zone lies generally in a plane 62 which is elevated above a base plane 64 which is defined by the bottom of the post member and the top of the insole of the shoe. The angle of the elevated bearing plane 62 relative to the base plane 64 determines the initial angulation of the plate member 16, and in turn the initial angulation (ordinarily inversion) of the rear foot: the angle of the wearer's rear foot lies generally along an axis which extends perpendicular to the focus of the heel cup, i.e., the central, generally lowermost portion of the heel cup.

In the example which is illustrated in FIG. 8, the bearing plane 62 extends at an angle of about 4° to the base plane 64. As a result, an axis 65 which is perpendicular to the focus of the heel cup of the plate member extends at an angle of about 4ø to an axis 66 which is perpendicular to the insole of the shoe. Hence, in this example, the assembly increases the inversion of the wearer's rear foot by about 4° from its natural position; in other words, if the natural inversion of the wearer's rear foot at heel strike is about 4°, the assembly will increase the total angle of inversion to about 8°. As will be described in greater detail below, this angulation is also adjustable in accordance with the present invention in order to meet the requirements of individual feet and/or uses.

FIGS. 6 and 7 also show the angled forward edge of the post member. As can be seen, the forward, medial corner 32 of the post member is positioned more forwardly than the lateral corner 34, so that a line 70 drawn between the two defines an angle α with a line 72 which extends perpendicular to the long axis of the assembly. The effect of this angulation is to form an extension 74 of the bearing surface on the medial side of the post member. This provides the rearward end of the arch area of the plate member with additional support and rigidity, so as to enable the assembly to employ a thin and somewhat resiliently flexible plate member for maximum comfort and control. It has found that an edge angle α of about 5°–15° is suitable for this purpose, with an angle of about 10°–15° being generally preferred.

The angled forward edge of the post member also results in an increased wall length at the front of the post, where this engages the insole, so as to create an enhanced "buttress" effect which helps to prevent the post member from sliding forwardly in the shoe. It will be understood, however, that some embodiments of the present invention the heel post member may lack the medial extension, i.e., the forward edge of the post may extend straight across or some angle other than those that have been described above. Furthermore, in some embodiments all or part of the forward edge of the post member may extend up the sagital plane incline from the rear foot towards the midfoot, as indicated by dotted line image 75 in FIG. 2, so as to form a somewhat upwardly inclined forward portion of the concave heel post which will react against the convex lower surface of the heel cup of the plate member so as to retain the plate member against shifting forwardly in the shoe.

Figure 9:
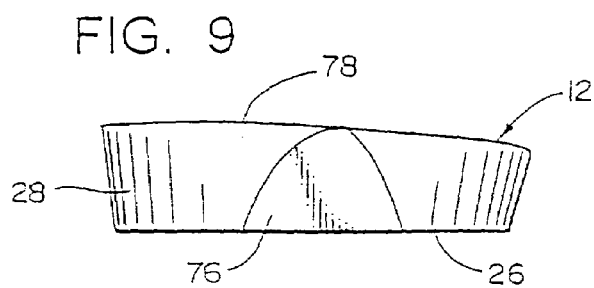
FIG. 9 is a rear, elevational view of the heel post member of FIGS. 6–8, showing the outer wall of the member around the heel end thereof.
Figure 10:
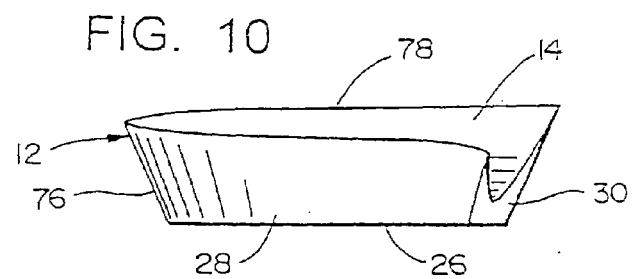
FIG. 10 is a right side elevational view of the right-foot post member of FIGS. 6–9, looking from the lateral towards the medial side thereof.
Figure 11:
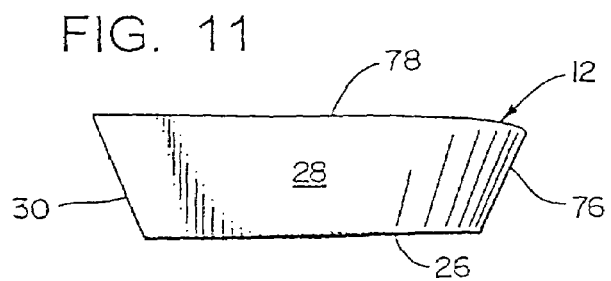
FIG. 11 is a left side elevational view of the heel post member of FIGS. 6–10.

The bottom and rear views in FIGS. 7 and 9 also show an angled cutaway or "skive" 76 which may be provided at the very heel end of the post member. As can be seen, the skive forms a generally flat, planar area which extends from the bottom surface 26 of the post member to near the upper edge 78 of the member, at a somewhat shallower angle than the remainder of the perimeter wall 28. The cutout provides additional clearance at the heel end of the post, so as to permit the post member to be fitted very closely and tightly within the heel counter in FIG. 2 (some space is shown between the rear of the post member and the heel counter of the shoe, however in most instances the post member will be installed tight against the heel counter. Again, however, it will be understood that this feature may not be present in some embodiments of the invention.

Figure 12:
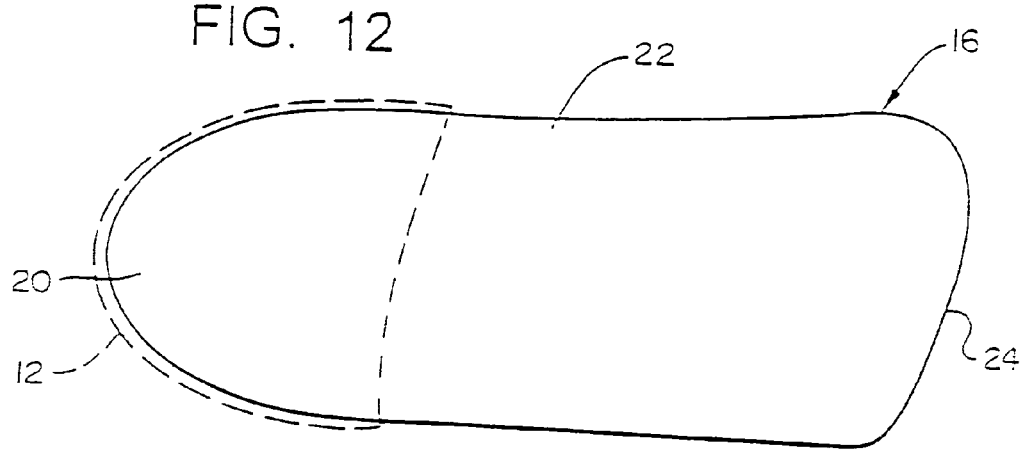
FIG. 12 is a top, plan view of a rigid, resiliently flexible plate member in accordance with the present invention, with the dotted line image showing the manner in which this fits into and engages the post member of FIGS. 6–11.
Figure 13:
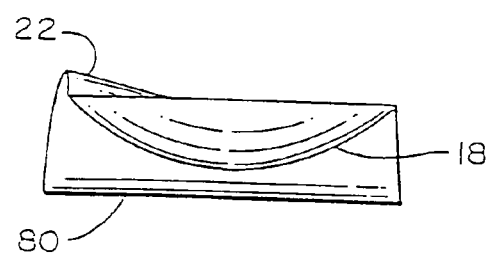
FIG. 13 is a rear, elevational view of the plate member of FIG. 12, showing the heel cup area thereof which engages the corresponding concave upper surface of the heel post member in accordance with the present invention.

FIGS. 12–13, in turn, show the plate member 16 in greater detail, and the manner in which this fits into the post member 12, as indicated by the broken line image in FIG. 12. FIG. 12 shows the post member being somewhat wider than the rear foot portion of the plate member, however, it will be understood that the width of the post member may be wider, equal to, or narrower than the rear foot portion of the plate member, depending on the design of the shoe, the nature of the individual foot, and other considerations.

From the standpoint of operation of the assembly, the principal features of the plate member are the generally convex rear foot bearing surface 18, which engages and pivots on the corresponding surface in the heel post member, and the generally flat lower surface 80 of the forefoot end 24, which extends parallel to the frontal plane when the medial forefoot comes to rest against the insole. The arch area and the contoured upper surface of the plate member are configured to engage and support the plantar surface of the wearer's foot, but may vary somewhat from one assembly to the next; for example, the arch portion may be more pronounced for assemblies which are designed for activities which require greater support in this area, or the arch portion may be more steeply or less steeply down-curved depending on the intrinsic anatomy of the individual foot or the type of shoe with which the device is to be used (e.g., a women's "pump" may require a more steeply down-curved arch portion than a low-heeled shoe).

c. Operation and Adjustment

Because the motion of the plate member, and therefore that of the wearer's foot, develops at the interface between the surfaces 14, 18 of the post and plate members, the function of the orthotic assembly of the present invention is not dependent on or affected by the contour of the shoe insole. The assembly is therefore able to function effectively in a wide variety of shoes, without requiring the painstaking and time-consuming grinding and shaping which is commonly involved in the fitting of prior art devices. Furthermore, the use of separate foot post and plate members eliminates any need to join these together using adhesives or other techniques.

Moreover, because both of the bearing surfaces (i.e., the top surface of the post member and the bottom surface of the plate member) are curved—unlike the generally flat surface of the insole—the assembly is able to generate a very uniform motion, without abrupt transitions or stops during or at the limit of travel.

The range of motion in the direction of eversion/pronation is controlled primarily by the forward end of the plate member coming to rest against the insole along the forefoot plane, the action of the convex bottom of the plate member coming up against the medial side of the concave post member, in turn, can be used to increase or decrease the resistance to the motion in the terminal phase of roll/pronation, thereby slowing the rate of pronation to a great or lesser degree: In general, a slower rate of roll in the terminal phase is preferably for a "loose", less stable foot, while a higher rate of pronation can be used with a more stable foot.

Figure 14:
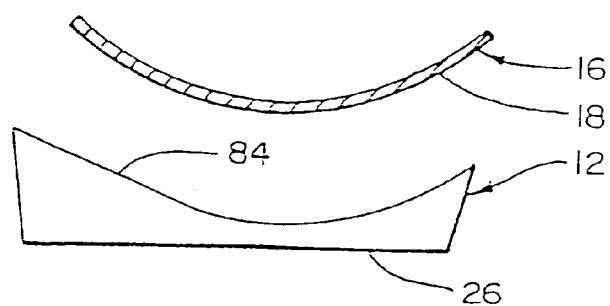
FIG. 14 is a cross-sectional view, looking from the rear forwardly, of a two-part orthotic assembly in accordance with an embodiment of the present invention in which the inclined medial side of the concave bearing surface serves to control the range of rearfoot motion which is allowed by the assembly.
Figure 15:
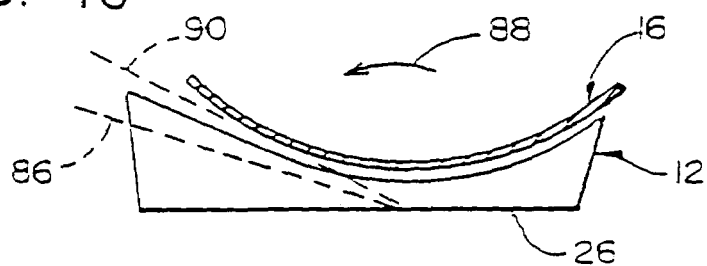
FIG. 15 is a cross-sectional view, similar to FIG. 14, showing the plate member fitted in engagement with the generally concave upper surface of the post member of FIG. 14.

For example, as can be seen in FIGS. 14–15, the rate of the pivoting motion or "roll" towards the medial side of the assembly can be controlled by means of the slope and/or height of a medial ramp portion 84 on the interior of the post member. The greater the incline of the ramp portion, the greater the resistance to pronation during the final phase of the gait cycle: Reducing the angle of the incline, as indicated by line 86 in FIG. 15, will allow a higher rate of rear foot motion in the medial direction, as indicated by arrow 88; conversely, a steeper incline, as indicated by line 90, will reduce the rate of motion.

Figure 16:
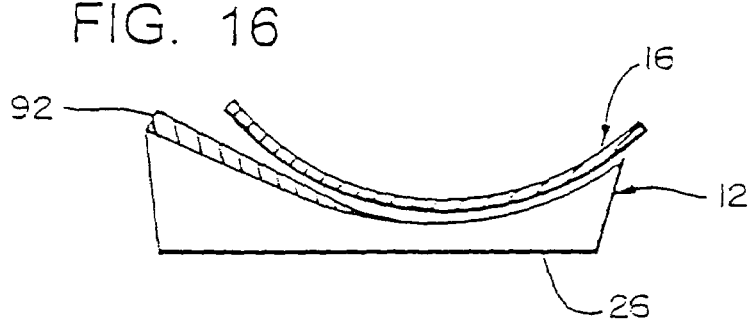
FIG. 16 is a rear, cross-sectional view, similar to FIG. 15, showing an embodiment of the invention in which the rearfoot motion is adjustable by means of wedges of selected sizes which are mountable within the interior of the concave bearing surface so as to control the pivoting motion of the plate member therein.

The assembly may also include means by which the inclination of the medial slope can be selectively adjusted. For example, as is shown in FIG. 16, one or more contoured wedges 92 may be adhered or otherwise mounted to the medial incline so as to selectively build this up and increase its slope. The wedge members may have a tapered contour, with the thin edge being positioned towards the bottom of the concave post surface 14 and the thicker edge being towards the edge of the post, or other shapes of wedges may be employed, depending on the application and the intended motion of the plate member. Moreover, a series of interchangeable wedge members may be provided, together with a "standard" shape of post member having a nominal medial incline to which the customer or a foot care practitioner can add one or more of the wedges depending on intended use, comfort or other needs of the individual foot, and so on. Consequently, this feature provides the device with a high degree of adjustability at minimal cost.

Figure 17:
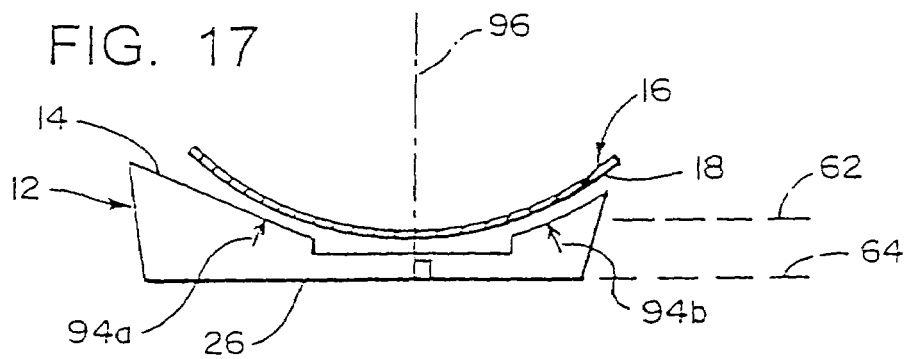
FIG. 17 is an end, cross-sectional view similar to FIG. 15, showing the initial angulation of the rearfoot which is provided by the two-piece assembly of the present invention.

As was noted above, the angle at which the assembly positions the wearer's rear foot during heel strike and the initial phases of the gait cycle can also be adjusted. For example, FIG. 17 shows a post member similar to that in FIG. 8, in which the bearing zone (as represented by arrows 94a, 94b on the medial and lateral sides of the heel cup) lies in a plane 62 which is generally parallel to the plane 64 of the post bottom/insole; in this case, an axis perpendicular to the heel cup generally matches an axis 96 perpendicular to the insole, i.e., the assembly adds little or no angulation of the rear foot relative to the insole.

Figure 18:
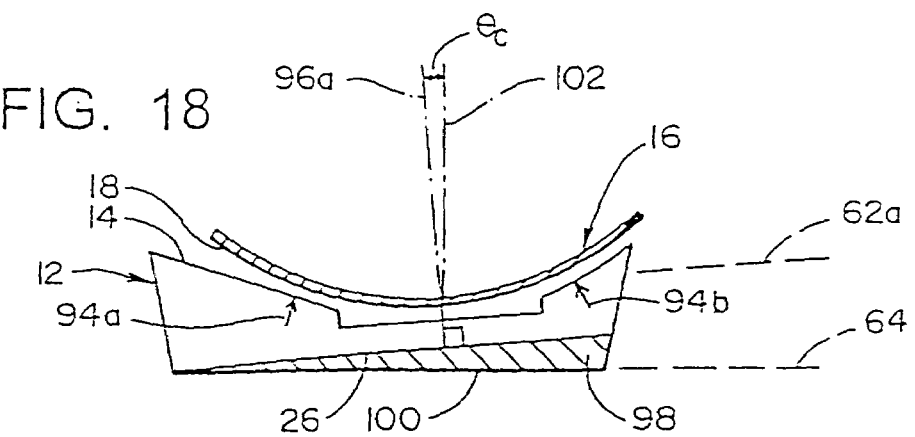
FIG. 18 is a rear, cross-sectional view, similar to FIG. 17, showing the manner in which the angulation of the rear foot is adjustable by adding one or more wedges to the planar bottom of the heel post member.
Figure 19:
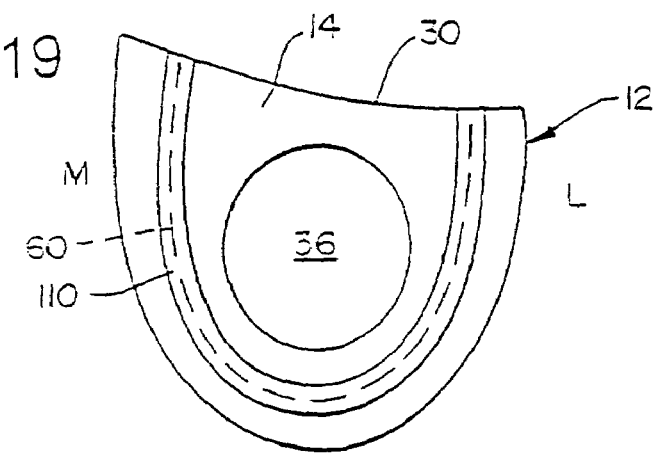
FIG. 19 is a top, plan view, similar to FIG. 6, showing an embodiment of the present invention in which the U-shaped bearing zone of the heel post member is enhanced or provided by a raised ridge which extends around the interior of the concave surface thereof.

Then, to selectively increase the angulation, a wedge or other support can be inserted under one side or the other of the post member. For example, as is shown in FIG. 18, a wedge member 98 may be mounted to the bottom of the post member with its thickest edge towards the medial side, so as to form a second, angled lower surface 100 which engages the insole so as to shift the plane of the bearing zone to an increased angle, as indicated at 62a. This in turn shifts angle of the plate member so as to increase the inversion of the rear foot, as indicated at 96a, by a predetermined angle $\theta_C$. If desired for a particular application, a wedge can be mounted to the bottom of the post member in a reverse manner, so as to increase eversion of the rear foot.

Accordingly, by mounting selected wedges to the bottom of the post member, the initial angulation of the rear foot can be adjusted as desired. While the amount of angulation will again depend on the nature of the individual foot and the intended use of the device, the angle $\theta_C$ will typically be in the range from about 0°–8°, with an angulation of about 4°–6° being common. Moreover, a series of adjustment wedges can be supplied for use with a standard post member so as to be able to increase the angulation of the rear foot by incremental amounts, e.g., 2°, 4°, 6°, 8°, and so on. Also, the wedges can be formed of a material having a stiffness greater than or comparable to that of the body of the post member, or they may be formed of a softer, more compressible material to provide more of a cushioning effect at the end of travel.

Figure 20:
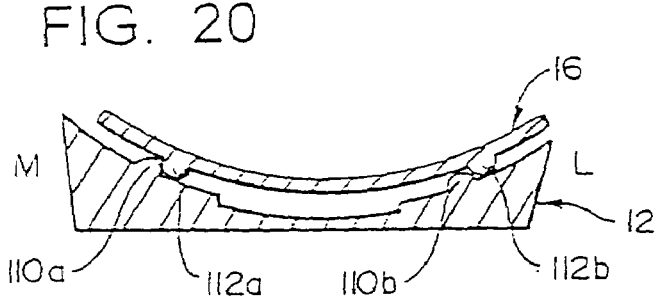
FIG. 20 is a rear, cross-sectional view, similar to FIG. 7, showing the manner in which the U-shaped ridge of the post member of FIG. 18 cooperates with a corresponding ridge on the bottom of the plate member so as to support the heel cup of the plate member at it predetermined initial angle.

FIGS. 19–22 illustrate embodiments of the invention in which adjustment of the rear foot angulation is achieved in a somewhat different manner. In these instances, the U-shaped bearing zone 60 is formed by a raised rib 110 which extends around the interior of the concave surface of the post member, this being shown somewhat exaggerated in the figures for purposes of illustration. As can be seen in FIG. 20, the medial and lateral portions 110a, 110b of the raised rib on the post member react against the medial and lateral portions 112a, 112b of the corresponding raised, downwardly projecting rib on the bottom of the plate member 16 to position the rear foot portion of the plate member at a predetermined degree of inversion at heel impact. Then, following heel impact, the plate member rotates on the post member for pronation of the foot, in the manner described above.

Figure 21:
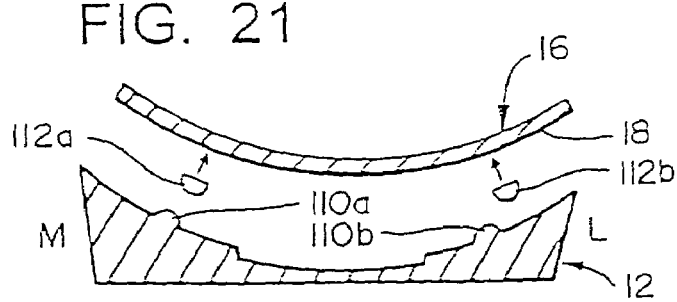
FIG. 21 is a cross-sectional view, similar to FIG. 20, showing an embodiment in which strips forming the ridge on the bottom of the plate member are selectively mountable thereon so as to adjust the initial angle of the heel cup.

The upper ridge 112 may be formed an integral part of the plate member, or as is shown in FIG. 21, the ridge may be made as a separate piece or pieces (i.e., the medial and lateral sides of the ridge 112a, 112b may be formed as two separate strips) which are mountable to the lower surface 18 of the plate member in a selected position, as indicated by the arrows in FIG. 21. For example, a practitioner may be provided with a standard post and plate member, and then the ridge or ridges 112a, 112b can be mounted in selected positions to provide a degree of inclination as needed by an individual foot.

Figure 22:
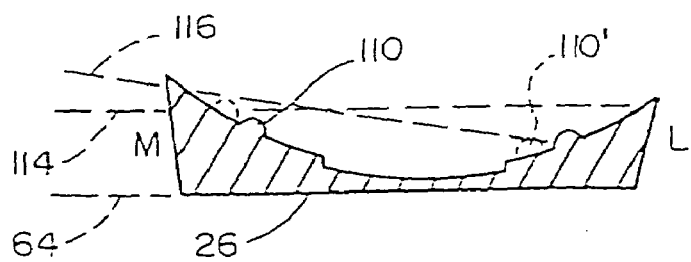
FIG. 22 is a cross-sectional view, similar to FIG. 20, showing the manner in which the initial angulation of the rear foot can be adjusted by adjusting the position of the U-shaped ridge within the post member.

As can be seen in FIG. 22, the angular adjustment can also be made by changing the position of the raised rib 110 within the interior of the post member. For example, in a first configuration, the U-shaped ridge 110 may be relatively level within the post member so as to define a somewhat horizontal support plane 114, thereby imparting only a small degree of additional angulation to the rear foot. To adjust this angulation, the position of the ridge may be shifted within the post member, as indicated by dotted line image 110', so that the ridge is higher on one side (e.g., the medial side) and lower on the other. This forms a second, angled support plane 116 which shifts the angle of the plate member and thereby increases/decreases the initial inversion of the rear foot by a predetermined amount. The raised ridge 110 may be molded or otherwise formed as an integral part of the post member, or this may be a separate piece which is adhered or otherwise mounted to the interior surface of the post member in a selected orientation.

FIGS. 23 and 24A–24B illustrate an embodiment of the present invention in which the plate member engages the stationary post member during use so as to hold the former in place against shifting forwardly in the shoe. In this embodiment, a transversely extending ridge 122 projects downwardly from the bottom surface 18 of the plate member 16, and is received in a corresponding channel or groove 120 which is formed in the upper surface of the post member. Since the post member 12 is mounted firmly to the insole 44 of the shoe, the engagement between the groove 122 and the ridge 120 prevents the plate member from shifting forwardly in the shoe as the person is walking, while still allowing the plate member to rock from side to side in order to generate the desired motion.

As can be seen in FIGS. 24A and 24B, the groove 122 and ridge 120 extend generally transverse to the long axis of the device/shoe, and the groove is preferably sized somewhat wider than the ridge so as to avoid friction which would interfere with movement between the two parts. Also, it will be understood that in some embodiments the ridge may be formed on the upper surface of the post member and the groove on the bottom of the plate member, the reverse of the arrangement which is shown in FIGS. 24A–24B.

FIGS. 25–33 illustrate an embodiment of the invention that provides an enhanced ability to control the direction and range of the rocking motion of the plate member. As can be seen in FIG. 25 and also FIGS. 26–27, the orthotic assembly 200 in accordance with this embodiment of the invention includes a concavely cupped heel post member 202 and substantially rigid plate member 204 that are generally similar in overall configuration to the corresponding members described above. However, as can be seen in FIGS. 25 and 26, the upper surface of the post member 202 is provided with a guide slot 206 that extends in a transverse direction and has closed lateral and medial ends 210, 212. The slot is comparatively narrow in the forward-to-rearward dimension, so that the main load-bearing interface formed by the concave upper surface 214 of the post is substantially preserved, but not so narrow as to compromise the strength of the peg or the stability of the connection that is formed with the plate member, as will be described below.

As can be seen in FIG. 27, the convex lower surface 216 of the plate member 204 is provided with a downwardly protruding peg 218 at a location beneath the heel end that corresponds to that of the guide slot in the post member. In the illustrated embodiment the peg is formed (e.g., molded) as an integral part of the rigid plate member, however, it will be understood that in some embodiments the peg member may be formed as a separate piece that is then mounted or attached to the bottom of the plate member.

The peg 218 has a front-to-rear dimension that corresponds to but is slightly smaller than the width of the guide slot 206, and a side-to-side dimension that is significantly smaller than the side-to-side length between the ends 210, 212 of the slot. This relationship enables the peg to move from side-to-side within the guide slot while being constrained against forward-to-rearward motion. Furthermore, the flat, face-to-face engagement between the vertical rearward and forward walls of the peg and the forward and rearward walls of the slot serves to form a sliding interface while securely holding the peg and plate in the slot.

In the illustrated embodiment, the depending peg portion of the plate is square, i.e., its front-to-rear and side-to-side dimensions are the same. It will be understood, however, that this will not necessarily be so in all cases. For example, the side-to-side dimension may be greater or smaller than the front-to-rear dimension, the latter generally being constrained to more-or-less match that of the guide slot. Moreover, the shape of the guide slot and peg may vary in other embodiments: For example, the slot may not include generally vertical walls along both its forward and rearward sides in all cases, since the primary resistance against the plate shifting forwardly in the shoe is generally provided by the forward wall of the slot. Furthermore, the ends of the slot and side walls of the peg portion may be rounded or oval, or have some other shape, rather than being flat as shown in FIGS. 26–27. Similarly, the slot may in some embodiments be a channel or track having a different cross-sectional contour rather than flat sides and bottom as shown, with the depending peg portion having a corresponding configuration, and still further there may be multiple pegs and slots. However, the preferred configuration that is shown in FIGS. 26–27 (i.e., a rectangular slot and a square/rectangular peg) is advantageous for durability and ease of manufacture, as well as for providing an effective arresting action in the event that motion of the plate member exceeds a predetermined limit.

Figure 29:
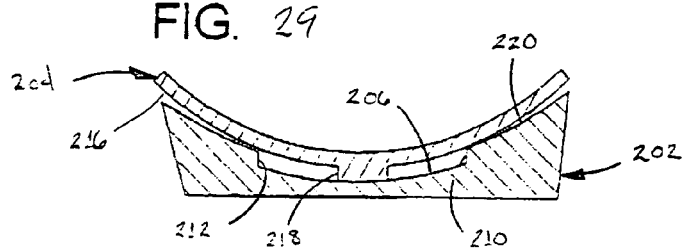
FIG. 29 is a cross-sectional view of the orthotic assembly of FIG. 25, taken along line 29—29 in FIG. 28, showing the relationship between the guide slot and peg portion in greater detail.
Figure 30:
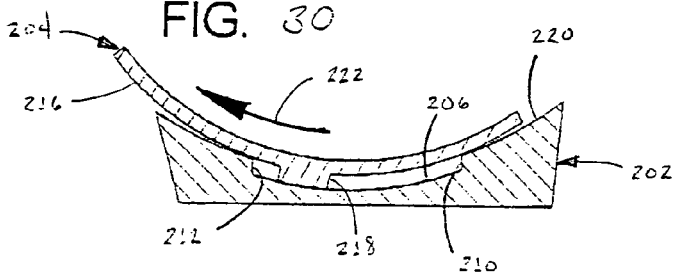
FIGS. 30–31 are cross-sectional views of the orthotic assembly of FIG. 25, similar to FIG. 29, showing the manner in which the guide slot of the heel member and depending peg portion of the plate member cooperate to direct the motion of the plate member as the plate member shifts towards the medial and lateral sides as the foot progresses through the gait cycle.
Figure 31:
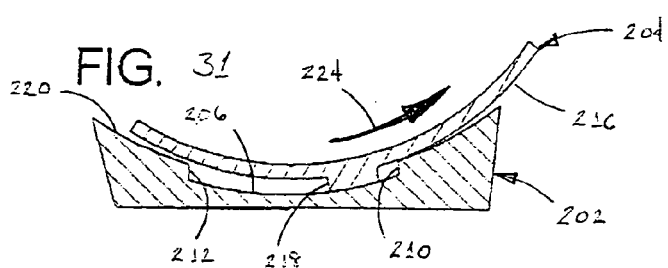

FIG. 28 shows the orthotic assembly 200 installed in an exemplary shoe 40. As can be seen, the depending peg 218 and guide slot 206 cooperate to hold the rigid plate against shifting in a longitudinal, forward-to-rearward direction. At the same time, as can be seen in FIGS. 29–31, the elongate transverse dimension of the slot permits the peg to slide in a transverse direction along with movement of the plate member: FIG. 29 shows the plate member 204 in a neutral position relative to the heel post member 202, with the depending peg 218 located more or less centrally between the end walls 210, 212 of the slot. FIGS. 30 and 31, in turn, illustrate the manner in which the guide slot cooperates with the peg 218 to allow the plate member 204 to rock in medial and lateral directions, as indicated by arrows 222, 224.

As can also be seen in FIGS. 29–31, the bottom surface of the guide slot is preferably concavely curved relative to a longitudinal axis of the assembly, with the bottom surface of the peg portion 218 having a matching convex curvature so that it bears directly against the bottom of the slot in order to form a load-bearing interface throughout the range of motion. The curvature of the bearing surfaces on the slot and peg portion corresponds generally to that of the convex/concave mating surfaces 216, 220 of the plate and the post members, so that downward loads are shared between the two sets of surfaces. Moreover, the support provided by the vertical interface of the surfaces on the peg and slot prevents the thin material of the plate member from flexing downwardly and deforming under the pressure of the heel, as might otherwise occur in this area and interfere with the intended movement of the members.

Figure 32:
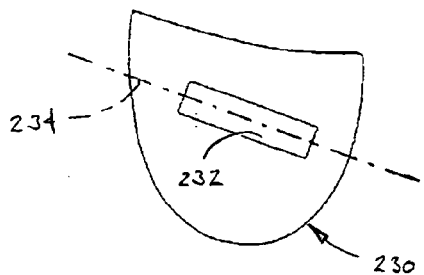
FIGS. 32–33 are top, plan views, similar to FIG. 26, showing the manner in which the guide slot of the heel post may be angled forwardly towards the medial or lateral side so as to direct the motions of the plate member accordingly, the angulation of the slots being shown somewhat exaggerated for ease of understanding.
Figure 33:
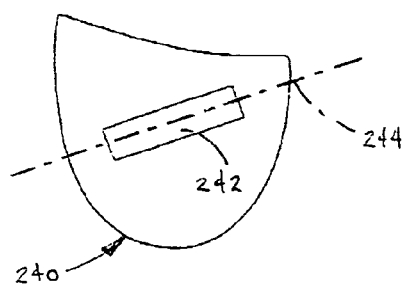

The post member 202 and plate member 204 therefore allow the orthotic assembly 200 to develop a lateral-to-medial rocking motion, similar to the other embodiments described above. However, the positive engagement formed by the guide slot and depending peg serves to precisely control the direction of the motion of the plate, thereby enabling the practitioner to exercise a precise degree of control over the motion of the foot. Moreover, the direction of motion can readily be adjusted by adjusting the direction of the slot. For example, the motion may be confined to a direction directly perpendicular to the long axis of the assembly, as is shown in FIGS. 25–27. FIG. 32, in turn, shows a heel post 230 having a guide slot 232 that (while still having a generally transverse orientation) extends along an axis 234 that is angled forwardly towards the medial side of the assembly. Similarly, FIG. 33 shows a post member 240 having a slot 242 that extends along an axis 244 that is angled in the opposite direction, i.e., forwardly towards the lateral side (it will be understood that the degree of angulation is somewhat exaggerated in FIGS. 32 and 33 for ease of illustration). In yet other instances, the slot may not extend along a straight-line axis, but instead may extend along a curved or multi-angled path, depending on the desired motion of the plate member and foot. The side walls of the peg portion, in turn, may be configured (e.g., angled) to match the guide slots, or may be cylindrical or rounded to allow a single configuration of peg to be used with slots having a variety of angles/configurations. The assembly therefore offers the practitioner not only the ability to precisely control the motions of the plate and foot, but the ability to direct those motions along a variety of paths and in a variety of directions as may be suitable for a particular application or to treat a particular condition of the foot.

It is to be recognized that various alterations, modifications, and/or additions may be introduced into the constructions and arrangements of parts described above without departing from the spirit or ambit of the present invention as defined by the appended claims.

What is claimed is:

1. An orthotic insert assembly for use with a shoe having an insole, comprising:
   a post member for substantially stationary mounting in said shoe, said post member comprising an elongate guide slot on an upper side thereof; and
   a thin, substantially rigid plate member for engaging a plantar surface of a wearer's foot in said shoe, said plate member being substantially free from attachment to said post member and comprising a heel cup formed in a heel portion thereof, and a peg portion depending from a lower surface of said heel portion for being received in said guide slot of said post member so that said peg portion cooperates with said guide slot to control and direct movement of said plate member atop said post member.

2. The orthotic insert assembly of claim 1, wherein said guide slot in said post member extends in a direction generally transverse to a long axis of said assembly, so that said peg portion cooperates with said guide slot to control a generally lateral-to-medial rocking movement of said plate member as a wearer's foot progresses through a gait cycle.

3. The orthotic insert assembly of claim 2, wherein said guide slot in said post member plate member comprises:
   a substantially vertically extending forward wall for reacting against said depending peg portion on said plate member so as to retain said plate member against shifting forwardly in said shoe.

4. The orthotic insert assembly of claim 3, wherein said guide slot in said post member further comprises:
   a substantially vertically extending rearward wall for reacting against said depending peg portion on said plate member so as to retain said plate member against shifting rearwardly in said shoe.

5. The orthotic insert assembly of claim 4, wherein said depending peg portion on said plate member comprises:

substantially vertically extending forward and rearward wall portions that bear against said vertically extending rearward and forward walls of said guide slot in face-to-face engagement so as to maintain said peg portion in said guide slot and retain said plate member against shifting forwardly and rearwardly in said shoe.

6. The orthotic insert assembly of claim 5, wherein said depending peg portion on said plate member has a forward-to-rearward width approximately equal to the forward-to-rearward width of said guide slot so that said peg portion forms a close-fitting sliding interfit therewith.

7. The orthotic insert assembly of claim 2, wherein said guide slot has a transverse length that is sufficient to permit said lateral-to-medial rocking movement of said plate member to extend over a predetermined range.

8. The orthotic insert assembly of claim 7, wherein said guide slot in said heel post member comprises:

medial and lateral end walls for engaging said depending post portion on said plate member so as to arrest said movement of said plate member outside of said predetermined range.

9. The orthotic insert assembly of claim 2, wherein said post member comprises an upper bearing surface having a generally concave curvature, and said heel portion of said plate member comprises a lower bearing surface having a generally convex curvature, so that said lower bearing surface of said plate member rests on said upper bearing surface of said post member in pivoting engagement therewith.

10. The orthotic insert assembly of claim 9, wherein said guide slot in said post member comprises:

a bottom wall having a concave curvature that generally parallels said concave curvature of said upper bearing surface of said post member.

11. The orthotic insert assembly of claim 10, wherein said depending peg portion on said plate member comprises:

a bottom wall having a convex curvature that generally matches said concave curvature of said bottom wall of said guide slot so as to form a load-bearing, sliding interface therewith.

12. The orthotic insert assembly of claim 2, wherein said guide slot is angled to direct said rocking movement of said plate member along a path that provides predetermined control over motions of said wearer's foot.

13. The orthotic insert assembly of claim 12, wherein said guide slot extends substantially perpendicular to said long axis of said assembly.

14. The orthotic insert assembly of claim 12, wherein said guide slot is angled forwardly towards a media side of said post member.

15. The orthotic insert assembly of claim 12, wherein said guide slot is angled forwardly towards a lateral side of said post member.

16. A method for positioning and controlling a wearer's foot in a shoe, comprising the steps of:

mounting a substantially stationary post member in a heel portion of a shoe, said post member comprising an elongate guide slot on an upper side thereof; and placing in said shoe a thin, substantially rigid plate member for engaging a plantar surface of a wearer's foot, said plate member being substantially free from attachment to said post member and comprising a heel cup formed in a heel portion thereof, and a peg portion depending from a lower surface of said heel portion that is received in said guide slot in said post member so that said peg portion cooperates with said guide slot to control and direct movement of said plate member atop said post member.

17. A shoe having an orthotic assembly, comprising:

a post member mounted in a substantially stationary position in said shoe, said post member comprising an elongate guide slot on an upper side; and a thin, substantially rigid plate member for engaging a plantar surface of a wearer's foot, said plate member being substantially free from attachment to said post member and comprising a heel cup formed in a heel portion thereof, and a peg portion depending from a lower surface of said heel portion that is received in said guide slot in said post member so that said peg portion cooperates with said guide slot to control and direct movement of said plate member atop said post member.

18. The shoe of claim 17, wherein said guide slot in said post member extends in a direction generally transverse to a long axis of said assembly, so that said peg portion cooperates with said guide slot to control a generally lateral-to-medial rocking movement of said plate member as a wearer's foot progresses through a gait cycle.

19. The shoe of claim 18, wherein said guide slot in said post member comprises:

a substantially vertically extending forward wall for reacting against said depending peg portion on said plate member so as to retain said plate member against shifting forwardly in said shoe.

20. The shoe of claim 17, wherein said post member comprises an upper bearing surface having a generally concave curvature, and said heel portion of said plate member comprises a lower bearing surface having a generally convex curvature, so that said lower bearing surface of said plate member rests on said upper bearing surface of said post member in pivoting engagement therewith.

21. The shoe of claim 20, wherein said guide slot in said post member comprises:

a bottom wall having a concave curvature that generally parallels said concave curvature of said upper bearing surface of said post member.

22. The shoe of claim 21, wherein said depending peg portion on said plate member comprises:

a bottom wall having a convex curvature that generally matches said concave curvature of said bottom wall of said guide slot so as to form a load-bearing, sliding interface therewith.

* * * * *